(12) United States Patent
Voellmicke

(10) Patent No.: US 7,909,833 B2
(45) Date of Patent: Mar. 22, 2011

(54) VERTEBROPLASTY DEVICE HAVING A FLEXIBLE PLUNGER

(75) Inventor: John Voellmicke, Cumberland, RI (US)

(73) Assignee: Depuy Acromed, Inc., Raynham, MA (US)

( * ) Notice: Subject to any disclaimer, the term of this patent is extended or adjusted under 35 U.S.C. 154(b) by 50 days.

(21) Appl. No.: 10/673,826

(22) Filed: Sep. 29, 2003

(65) Prior Publication Data

US 2005/0070912 A1     Mar. 31, 2005

(51) Int. Cl.
  *A61B 17/58*      (2006.01)
  *A61F 2/00*       (2006.01)
(52) U.S. Cl. ....................................................... 606/94
(58) Field of Classification Search ............... 606/92–94
  See application file for complete search history.

(56) References Cited

U.S. PATENT DOCUMENTS

| 833,044 | A | | 10/1906 | Goodhugh | |
|---|---|---|---|---|---|
| 3,354,882 | A | * | 11/1967 | Coanda | 604/222 |
| 4,064,566 | A | * | 12/1977 | Fletcher et al. | 128/898 |
| 4,472,141 | A | | 9/1984 | Dragan | |
| 4,493,704 | A | * | 1/1985 | Beard et al. | 604/154 |
| 4,645,488 | A | * | 2/1987 | Matukas | 604/59 |
| 4,653,489 | A | | 3/1987 | Tronzo | |
| 4,769,011 | A | | 9/1988 | Swaniger | |
| 4,801,263 | A | | 1/1989 | Clark | |
| 4,865,591 | A | * | 9/1989 | Sams | 604/186 |
| 5,145,250 | A | | 9/1992 | Planck et al. | |
| 5,681,285 | A | * | 10/1997 | Ford et al. | 604/151 |
| 5,800,390 | A | * | 9/1998 | Hayakawa et al. | 604/93.01 |
| 6,241,734 | B1 | | 6/2001 | Scribner et al. | |
| 6,348,055 | B1 | | 2/2002 | Preissman | |
| 6,402,758 | B1 | | 6/2002 | Tolson | |
| 6,439,439 | B1 | * | 8/2002 | Rickard et al. | 222/391 |
| 6,746,430 | B2 | * | 6/2004 | Lubrecht | 604/230 |
| 6,770,079 | B2 | * | 8/2004 | Bhatnagar et al. | 606/94 |
| 7,011,649 | B2 | * | 3/2006 | De La Serna et al. | 604/197 |
| 7,326,203 | B2 | | 2/2008 | Papineau | |
| 2002/0049449 | A1 | * | 4/2002 | Bhatnagar et al. | 606/94 |
| 2004/0064136 | A1 | * | 4/2004 | Papineau et al. | 606/41 |

FOREIGN PATENT DOCUMENTS

| EP | 1060731 | 12/2000 |
|---|---|---|
| WO | WO 98/56301 | 12/1998 |
| WO | WO 00/54705 | 9/2000 |
| WO | 02/064062 | 8/2002 |
| WO | 2005051212 | 6/2005 |

OTHER PUBLICATIONS

International Search Report from PCT/US04/30953 dated May 11, 2005.
Jensen, "Percutaneous Polymethylmethacrylate Vertebroplasty in the Treatment of Osteoporotic Certebral Body Compression Fractures: Technical Aspects", Am J Neuroradiology, 1997, pp. 1897-1904, vol. 18.

* cited by examiner

*Primary Examiner* — Anu Ramana

(57) ABSTRACT

A device for injecting bone cement is provided. The device has a flexible delivery tube and a flexible plunger.

18 Claims, 2 Drawing Sheets

VERTEBROPLASTY DEVICE HAVING A FLEXIBLE PLUNGER

BACKGROUND OF THE INVENTION

In vertebroplasty, the surgeon seeks to treat a compression fracture of a vertebral body by injecting bone cement such as PMMA into the fracture site. In one clinical report, Jensen et al., *AJNR:* 18 Nov. 1997, Jensen describes mixing two PMMA precursor components in a dish to produce a viscous bone cement; filling a 10 ml syringe with this cement, injecting the cement from the larger syringe into a plurality of smaller 1 ml syringes, and finally delivering the viscous cement into a desired area of the vertebral body through needles attached to the smaller syringes.

In order to insure that the injected cement does not travel far from its intended placement location, fluoroscopy is often used by the clinician to monitor the location of the injected cement. However, since delivering the cement by a simple syringe requires placing the clinician's hand in the fluoroscopy field, delivering the cement under direct fluroroscopy would cause the clinician to be exposed to significant x-ray radiation within a fluoroscopy field produced by a fluoroscope. Thus, in order to reduce such exposure, the clinician often performs this procedure when the fluoro is turned off, and only monitors the cement location intermittently when safely outside the range of the fluoroscopy field.

In response to these concerns, techniques for allowing the clinician to remain outside of the fluoro field have been developed. These techniques typically involve the use of a long delivery tube, whereby the proximal end of the tube extends from a cement injection means and the distal end is coupled to a hollow bore cannula inserted into the vertebral body. The delivery tube is used as a conduit for delivering the bone cement from the injection means to the cannula for injection into the vertebral body. The additional length of the delivery tube allows the clinician to perform the vertebroplasty procedure at a distance outside the fluoro field.

U.S. Pat. No. 6,348,055 ("Preissman") discloses a cement delivery system suitable for vertebroplasty involving a high pressure injection gun that delivers cement through a flexible tube and into a rigid cannula inserted in the vertebral body. Preissman also discloses that a stylet made of steel or other suitable metal may be inserted into the cannula for the purpose of penetrating hard tissue. See Priessman at col. 6, lines 28-55.

Preissman does not discloses a flexible stylet, nor does Preissman discloses inserting the stylet into the flexible delivery tube.

U.S. Pat. No. 6,241,734 ("Scribner") discloses a vertebroplasty cement delivery system having a series of cannulae and a tamping instrument designed to deliver cement into the patient at a pressure of no greater than about 360 psi. The tamping instrument is generally made from rigid, inert plastic or metal material. See Scribner at col. 11, lines 17-18.

PCT Published Patent Application No. WO 00/54705 ("Bhatnagar") also discloses a vertebroplasty cement delivery system having a series of cannulae and a plunger designed to deliver cement into the patient. Bhatnagar discloses that the injection device can be fabricated from any of a variety of materials, which are compatible for use as surgical instruments, including metallic materials and non-metallic materials such as thermoplastics, ceramic materials, carbon fiber materials and composite materials. See Bhatnagar at page 19, lines 13-20.

U.S. Pat. No. 4,769,011 ("Swaniger") discloses a syringe apparatus comprising a flexible plunger stem slidably received in barrel. Because this device was designed to delivery granular substances during alveolar ridge augmentation and repair, the barrels are preformed to described arcs similar to that of the alveolar ridge. Swaniger discloses that the barrel is made of glass. See Swaniger at col. 6, line 7.

In sum, all of the prior art systems that use both a delivery tube and stylet disclose either a rigid delivery tube or a rigid stylet.

SUMMARY OF THE INVENTION

The present inventor has noted that the conventional systems having rigid delivery tubes are often limited in tube length because the rigid nature of the delivery tube will tend to produce a high torque upon the inserted cannula when the delivery tube is moved off the axis of the cannula.

The present inventor has further noted that the conventional systems having a flexible tube use a proximally located injection means to deliver cement through the delivery tube. However, the pressure drop associated with the length of tube requires that the clinician provide more force to deliver the viscous cement.

In accordance with the present invention, the present inventor has developed a cement delivery system suitable for vertebroplasty containing both a flexible delivery tube and a flexible plunger.

In preferred embodiments, the cement is provided in the distal end of the bore of the delivery tube, while the plunger is provided in the proximal portion of the delivery tube. Activating the injection means distally advances the plunger through the delivery tube, thereby forcing the distally located cement to move out of the distal end of the delivery tube and into the cannula seated in the vertebral body.

Because each of the plunger and tube components is flexible, their off-axis movement does not produce an unreasonably high torque upon the seated cannula. Accordingly, each may be made to a length sufficiently long so that the proximally-located injection means, and therefore, the clinician may be located far from the fluoroscopy field.

Therefore, in accordance with the present invention, there is provided a device for injecting bone cement, comprising:
  a) a flexible delivery tube having a proximal end portion, a distal end portion, and an inner bore defining an inner diameter,
  b) a flexible plunger having a distal end portion sized for slidable reception in the bore, and
  c) an advancement means for distally advancing the plunger, the means located adjacent the proximal end portion of the flexible delivery tube.

Also in accordance with the present invention, there is provided a method of delivering bone cement, comprising the steps of:
  a) providing a flexible delivery tube having a proximal end portion, a distal end portion, and an inner bore defining an inner diameter,
  b) filling the bore of the flexible delivery tube with a viscous bone cement, and
  c) distally advancing a flexible plunger through the bore, thereby ejecting the viscous bone cement from the bore.

DETAILED DESCRIPTION OF THE INVENTION

Figure 1:
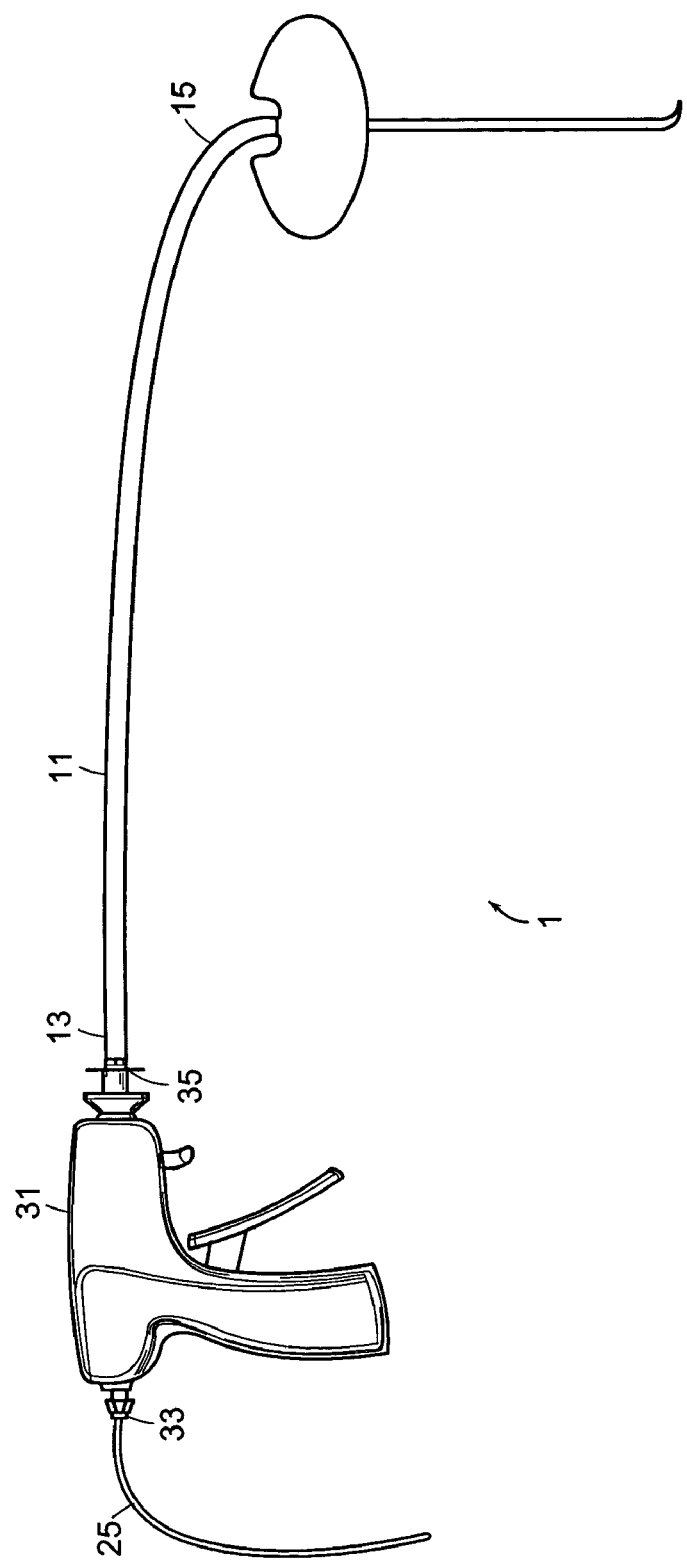
FIG. 1 discloses a side-view of the injection device of the present invention.
Figure 2:
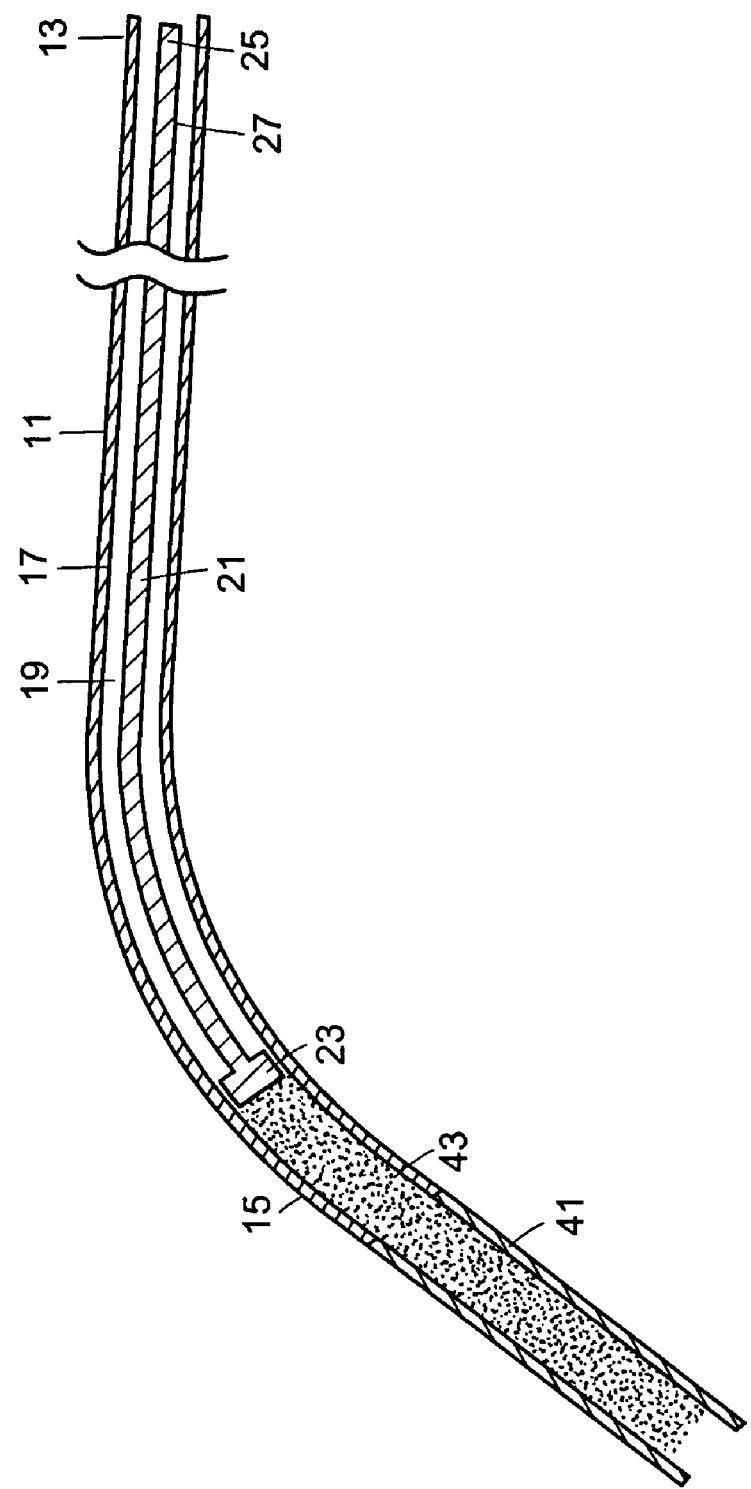
FIG. 2 discloses an axial-cross section of a distal portion of the injection device of the present invention a portion of which is filled with cement.

Now referring to FIGS. 1 and 2, there is provided a device 1 for injecting bone cement, comprising:
a) a flexible delivery tube 11 having a proximal end 13, a distal end 15, and an inner surface 17 defining a bore 19,
b) a flexible plunger 21 having a distal end portion 23 sized for slidable reception in the bore and a proximal end portion 25,
c) an advancing means 31 for distally advancing the plunger, the means located adjacent the proximal end of the flexible delivery tube.

As noted above, the delivery tube is made to be flexible so as to allow it to be made to a length sufficiently long so as to allow the surgeon to remain outside the fluoroscopy field and to minimize any torque at its distal end produced by off-axis movement relative to the cannula. Preferably, its inner surface is sterile in order to minimize infection.

Preferably, the tube is made of a non-compliant material that will reduce the amount of cement oozed from the tube into the patient after plunger actuation. A preferred material of construction for both the delivery tube and plunger is PEEK, which has good chemical resistance and flexibility.

In some embodiments, the inner surface of the flexible delivery tube defines an inner diameter that is small (i.e., on the order of 0.05-0.2 inches). When the inner diameter is so small, the clinician need not provide large forces in order to move the cement through the tube.

In some embodiments, the inner diameter of the flexible delivery tube is relatively large (i.e., on the order of at least 0.3 inches). When the inner diameter is so large, the pressure applied to the cement contained with the tube is relatively low (as the pressure drop over the tube length is lower for a constant force), thereby reducing the chances of extravasation from the vertebral body.

In some embodiments, the inner diameter of the flexible delivery tube is between 50% and 200% of the inner diameter 43 of the cannula 41. In this condition, the drag upon the cement is essentially equal in the two regions, thereby providing ergonomic efficiency. In more preferred embodiments, the inner diameter of the flexible delivery tube is between 80% and 120% of the inner diameter of the cannula. More preferably, the inner diameter of the flexible delivery tube is essentially equal to the inner diameter of the cannula.

In some embodiment, the entire length of the delivery tube is flexible. This provides for ease of manufacturing and minimizes the chances of producing problematic torque. In some embodiments, however, only the distal portion of the delivery tube is flexible. This embodiment still minimizes torque at the cannula connection.

In preferred embodiments, the length of the flexible delivery tube is at least 20 cm, more preferably 20 cm and 40 cm. In this range, the clinician may be placed safely outside the fluoroscopy field while still maintaining a relatively small device length.

Although surgeons in the 1990's were injecting up to 17 cc of cement into a single vertebral body, in recent years, there is a distinct trend towards reducing the volume of cement injected into any one vertebral body. Today, some surgeons advocate injecting as little as 4 cc's of cement into a single vertebral body. Accordingly, the volume define by the bore of the flexible delivery tube is preferably less than 4 cc, more preferably less than 3 cc, more preferably less than 2 cc.

In some embodiments, the flexible delivery tube has a length of about 30 cm and has an inner diameter of about 2.0 mm (about 0.080"), thereby producing a bore having a volume of about 1 cc. Such a small volume bore can be easily filled with cement immediately after the cement precursors are mixed, when viscosity of the mixture is still very low. The long length of the tube also keeps the surgeon's hands out of the fluoroscopic field during the procedure. Since the surgeon would need to deliver at least 4 cc of cement during the procedure, in practice, the surgeon would need to fill four of these flexible delivery tubes with cement, put three of these filled tubes in chilled saline, and load one of the filled tubes into the device of the present invention. After delivering the cement from the delivery tube into the patient's vertebral body, the surgeon would need to sequentially remove the remaining chilled tubes from the saline bath and likewise inject their contents into the patient's vertebral body.

The flexible tube of the present invention can further comprise at least one removable air-vent cap (not shown). The cap is sized to fit on one end of the tube and allows air to pass therethrough while preventing cement leakage therethrough. When the caps are placed on each end of the filled flexible delivery tube, the leakproof filled tube can then be placed in a chilled bath in order to slow the polymerization rate of the cement contained therein.

The plunger is designed for slidable reception within the flexible delivery tube, and has a distal portion 23 having a first diameter essentially equal to the inner diameter of the flexible delivery tube.

In some embodiments, the plunger is adapted to enhance its coupling to the advancing means. In some embodiments, a portion of the outer surface of the plunger is textured to enhance its coupling to the advancing means. In some embodiments, the outer surface 27 of the proximal end of the plunger is provided with ratchet teeth that compliment a pawl provided on the advancing means. Together, these create a ratchet-and-pawl mechanism suitable for advancing the plunger.

In some embodiments, the plunger has substantially a cylinder shape and so has a single diameter along substantially its entire length. This embodiment is desirable for manufacturing simplicity. However, high surface area contact of the plunger with the inner diameter of the flexible delivery tube may be so substantial as to undesirably increase the force needed to advance the cement through the distal end of the flexible delivery tube.

Accordingly, in other embodiments, as in FIG. 1, the distal end portion 23 of the plunger has a diameter that is larger than the proximal end portion 25 of the plunger. In this embodiment, the relatively lower surface area contact of the plunger with the inner diameter of the flexible delivery tube desirably minimizes the force needed to advance the cement through the distal end of the flexible delivery tube.

In some particularly preferred embodiments, the inner diameter of the flexible delivery tube is on the order of 2-3 mm, and so the diameter of the distal end portion of the flexible plunger will be slightly less than that value in order to both slide within the tube and to prevent backflow of the cement.

In some embodiments, as in FIG. 1, the flexible plunger takes the form of a wire or monofilament. In some embodiments, the wire can enter a proximal end portion 33 of the handheld gun 31, advanced through the gun, and exit a distal portion 35 of the gun by the same advancing means. Individual lengths of wire (each equal to the length of the tube) can be sequentially combined to make a virtual spool of the wire. In some embodiments, a first wire from the spool can be slowly fed into the flexible tube, advanced through the tube up to the cannula, and then cut at its proximal end when the emptied flexible tube is removed, thereby allowing the next length of wire to advance the next bolus of cement in the next filled delivery tube.

The advancing means can be any means that distally advances the plunger through the flexible delivery tube. Preferably, the advancing means is provided with mechanical advantage. In some embodiments, the advancing means can include a ratchet and pawl mechanism, wherein a set of ratchet teeth is provided on the outer surface of the plunger and a pawl is provided upon a proximally located gun. In some embodiments, the advancing means can comprise a threaded cylinder. In other embodiments, the advancing means can be designed in accordance with any advancing means disclosed in U.S. Ser. No. 10/259,689, the specification of which is incorporated by reference in its entirety. In some embodiments, the advancing means can be in the form of a hand-operated gun provided with at least a portion of a ratchet mechanism.

In some embodiments, the advancing means comprises a gear drive. Gear drives typically provide a large mechanical advantage to the user. In some embodiments, the gear drive drives a pair of wheels disposed on and contacting opposite sides of the flexible plunger. When these opposed wheels are rotated in opposite directions, their contact with the plunger drives the plunger distally.

In some embodiments, sealing connection between the proximal end of the cannula and the distal end of the flexible delivery tube is accomplished by complimentary Luer fittings. Likewise, in some embodiments, sealing connection between the distal end of the cannula and the proximal end of the advancing means is accomplished by complimentary Luer fittings.

In some embodiments, the device of the present invention is used to deliver bone cement into a fractured vertebral body. The bone cement may be any material typically used to augment vertebral bodies, including acrylic-based bone cements (such as PMMA-based bone cements), pastes comprising bone particles (either mineralized or demineralized or both; and ceramic-based bone cements (such as HA and TCP-based pastes). In some embodiments, the bone cement comprises the bone cement disclosed in WO 02/064062 (Voellmicke).

In some embodiments, the bore is filled with a bone cement having a temperature of less than room temperature. This condition lowers the polymerization rate of the cement and so extends the working time of the cement. Preferably, the cement is chilled to a temperature of no more than 10° C.

First, under fluoroscopic guidance, the surgeon percutaneously places into a fractured vertebral body a needle comprising the cannula of the present invention and a stylet. The stylet is then removed from the patient, thereby leaving the cannula in place as the means for delivering the cement from the flexible delivery tube to the fracture site.

The flexible delivery tube of the present invention may be filled with viscous cement by any number of conventional filling procedures. In some embodiments, the cement precursors can first be mixed in a separate mixing syringe or other mixing device, such as the device disclosed in WO 02/064062 (Voellmicke) in order to mix and deliver the cement quickly and easily and with little fume exposure. The mixed cement is then transferred from the mixing device into a plurality of flexible delivery tubes, each tube having an endcap affixed thereto on its distal end. The surgeon injects the cement into the fill (or open) end of the flexible delivery tube until the cement reaches vented cap, and then places another vented cap on the fill end of the tube in order to insure the cement remains within the tube.

In some embodiments wherein a large number of delivery tubes are filled, it is advantageous to chill the unused filled tubes prior to use in order to slow the polymerization reaction that cures the cement. In some embodiments, the tubes are rapidly filled at the beginning of the procedure, capped, and then placed in a sterile saline ice bath to slow the polymerization of the cement. In some embodiments, the working time can be extended by chilling for a period of between 30 minutes and 60 minutes.

Next, the delivery tubes are sequentially connected between the cannula and the handheld gun via luer fittings. The advancing means located on the gun is then activated to distally advance the plunger, thereby pushing the cement located in the flexible delivery tube into the cannula and ultimately the patient.

I claim:

1. A device for injecting bone cement, comprising:
   a) a flexible delivery tube having a proximal end portion, a distal end portion, and an inner bore defining an inner diameter,
   b) a flexible plunger in the form of a wire or a monofilament, the flexible plunger having a distal end portion slidably received in the bore of the flexible delivery tube,
   c) an advancement means for distally advancing the plunger, the means attached to the proximal end portion of the flexible delivery tube, and
   d) a cannula having a proximal end attached to the distal end portion of the flexible delivery tube, the cannula adapted to be seated in a vertebral body.

2. The device of claim 1 wherein the inner bore is sterile.

3. The device of claim 1 wherein the tube is made of PEEK.

4. The device of claim 1 wherein the inner diameter of the flexible delivery tube is between 0.05 and 0.2 inches.

5. The device of claim 1 wherein the diameter of the flexible delivery tube is between 50% and 200% of the diameter of the cannula.

6. The device of claim 1 wherein the flexible delivery tube has a length of at least 20 cm.

7. The device of claim 1 wherein the flexible delivery tube has a length of between 20 cm and 40 cm.

8. The device of claim 1 wherein the bore of the flexible delivery tube has a volume of less than 4 cc.

9. The device of claim 1 wherein the bore of the flexible delivery tube has a volume of less than 3 cc.

10. The device of claim 1 wherein the bore of the flexible delivery tube has a volume of less than 2 cc.

11. The device of claim 1 wherein the bore is filled with a bone cement having a temperature of less than room temperature.

12. The device of claim 1 wherein the bore is filled with a bone cement having a temperature of no more than 10° C.

13. The device of claim 1 wherein the bore is filled with a bone cement comprising an acrylic-based bone cement.

14. The device of claim 1 wherein the bore is filled with a bone cement comprising a paste comprising bone particles.

15. The device of claim 1 wherein the bore is filled with a bone cement comprising a ceramic-based bone cement.

16. The device of claim 1 wherein the plunger has a proximal end portion and a distal end portion, the distal end portion having an enlarged portion diameter and a second proximal end portion diameter, wherein the first distal end portion diameter is greater than the second proximal end portion diameter.

17. The device of claim 1 wherein the advancement means comprises a threaded cylinder.

18. The device of claim 1 wherein the advancement means comprises a gear drive.

* * * * *

UNITED STATES PATENT AND TRADEMARK OFFICE
CERTIFICATE OF CORRECTION

| | | |
|---|---|---|
| PATENT NO. | : 7,909,833 B2 | Page 1 of 1 |
| APPLICATION NO. | : 10/673826 | |
| DATED | : March 22, 2011 | |
| INVENTOR(S) | : Voellmicke | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Eleventh Day of October, 2011

David J. Kappos
*Director of the United States Patent and Trademark Office*